US006255056B1

(12) United States Patent
Eyre

(10) Patent No.: US 6,255,056 B1
(45) Date of Patent: Jul. 3, 2001

(54) CARTILAGE RESORPTION ASSAYS

(75) Inventor: David R. Eyre, Seattle, WA (US)

(73) Assignee: Washington Research Foundation, Seattle, WA (US)

( * ) Notice: Subject to any disclaimer, the term of this patent is extended or adjusted under 35 U.S.C. 154(b) by 0 days.

(21) Appl. No.: 09/335,098

(22) Filed: Jun. 17, 1999

Related U.S. Application Data

(60) Provisional application No. 60/089,823, filed on Jun. 19, 1998.

(51) Int. Cl.$^7$ ..................................................... G01N 33/53
(52) U.S. Cl. ........................... 435/7.1; 435/7.7; 435/7.9; 435/975; 436/518; 530/328
(58) Field of Search .................................. 435/7.21, 7.7, 435/7.9, 975, 7.1; 436/518; 530/387.1, 387.9, 388.1, 388.9, 389.1, 389.8, 391.1, 391.3, 350, 323, 324–329

(56) References Cited

U.S. PATENT DOCUMENTS

| | | |
|---|---|---|
| 4,628,027 | 12/1986 | Gay . |
| 4,973,666 | 11/1990 | Eyre . |
| 5,140,103 | 8/1992 | Eyre . |
| 5,300,434 | 4/1994 | Eyre . |
| 5,316,914 | 5/1994 | Oshima et al. . |
| 5,320,970 | 6/1994 | Eyre . |
| 5,476,765 * | 12/1995 | Wang ........................................ 435/5 |
| 5,702,909 | 12/1997 | Eyre . |
| 5,817,755 | 10/1998 | Eyre et al. . |

FOREIGN PATENT DOCUMENTS

| | | |
|---|---|---|
| 0 505 210 A2 | 3/1992 | (EP) . |
| 0 699 752 A2 | 3/1996 | (EP) . |
| 0 718 309 A1 | 6/1996 | (EP) . |
| WO 88/08980 | 11/1988 | (WO) . |
| WO 89/04491 | 5/1989 | (WO) . |
| WO 89/12824 | 12/1989 | (WO) . |
| WO 91/08478 | 6/1991 | (WO) . |
| WO 92/21698 | 12/1992 | (WO) . |
| WO 94/03813 | 2/1994 | (WO) . |
| WO 94/14070 | 6/1994 | (WO) . |
| WO 94/14844 | 7/1994 | (WO) . |
| WO 94/18563 | 8/1994 | (WO) . |
| WO 95/04282 | 2/1995 | (WO) . |
| WO 95/08115 | 3/1995 | (WO) . |
| WO 96/12193 | 4/1996 | (WO) . |
| WO 96/36645 | 11/1996 | (WO) . |

OTHER PUBLICATIONS

Otter, A., et al., Biopolymers 33:1443–1459, 1993.
Eyre, D.R., et al., Cross–linked telopeptides from collagen types I, II and III in human urine, Bone Miner. Res. 11(S1): S413, 1996.
Atley, L., et al., A selective inhibitor of collagenase–3 blocks the release of hydroxyproline and a metalloproteinase specific neoepitope, coll II CTx, from bovine collagen exposed to IL–1α, Arth. Rheum. 40(9S):584, 1997.
Atley, L., et al., Matrix metalloproteinase–mediated release of immunoreactive telopeptides from cartilage type II collagen, Trans. Orthop. Res. Soc., New Orleans, 1998.
Moskowitz, R.W., et al., Type II collagen C–telopeptide is a marker for cartilage degradation in familial osteoarthritis, Amer. Coll. Rheum., San Diego, CA, Nov. 8–12, 1998.
Eyre, D.R., et al., Biochemical markers of bone and cartilage collagen degradation, Combined Orthopaedic Research Societies Meeting, Vittel, France, Sep. 28–30, 1998.
Sheridan, C., Osteometer targets collagen for osteoporosis, arthritis tests, BioWorld International, p. 3, Dec. 3, 1997.
Atley, L.M., et al., Collagen type II cross–linked telopeptides, a promising marker for cartilage degradation in arthritis, Combined Orthopaedic Research Societies Meeting, Hamamatsu, Japan, 1998.

* cited by examiner

*Primary Examiner*—Jeffrey Stucker
(74) *Attorney, Agent, or Firm*—Christensen O'Connor Johnson Kindness PLLC

(57) ABSTRACT

Immunoassays for measuring type II collagen (cartilage) resorption in vivo employ either one or two antibodies. A first antibody binds to EKGPDP (SEQ ID NO:2) but not to EKGPDPLQ (SEQ ID NO:10), where the K symbols refer to lysine or preferably to cross-linking 3-hydroxypyridinium residues. Measurement of analyte binding to the first antibody in serum provides an indication of unmineralized cartilage resorption in vivo. A second antibody binds to EKGPDPLQ (SEQ ID NO:10) but not to EKGPDP (SEQ ID NO:2). Measurement of analyte binding to the second antibody in serum provides an indication of mineralized cartilage resorption in vivo. An indication of total (unmineralized and mineralized) cartilage resorption in vivo is provided by either measurement of analyte binding to the first antibody in urine, or by measurement of the total analyte binding to the first and second antibodies in serum.

18 Claims, No Drawings

CARTILAGE RESORPTION ASSAYS

This is a continuation-in-part of provisional application Ser. No. 60/089,823, filed Jun. 19, 1998. +gi This invention was made with government support under one or more of grants AR 37318 and AR 36794 awarded by the National Institutes of Health. The government has certain rights in the invention.

FIELD OF THE INVENTION

The invention relates to assays for detecting cross-linked telopeptide analytes indicative of type II collagen (cartilage) resorption in vivo, and in particular provides immunoassays for measuring and distinguishing between resorption of unmineralized cartilage and mineralized cartilage, and for measuring total cartilage resorption in vivo.

BACKGROUND OF THE INVENTION

Reference is made to the applicant's prior U.S. Pat. Nos. 4,973,666, 5,140,103, 5,300,434, 5,320,970, 5,817,755, and 5,702,909, which are incorporated by reference herein.

Immunoassays are known for detecting telopeptide analytes indicative of collagen resorption in vivo. Examples of such type I collagen assays for measuring bone resorption include: WO 89/04491 (Eyre); WO 89/12824 (Robins); WO 91/08478 (Eyre); Ep 0505210 A2 (Risteli & Risteli); WO 92/21698 (Eyre); WO 94/03813 (Naser et al.); WO 94/14844 (Baylink); WO 95/04282 (Naser et al.); WO 95/08115 (Qvist & Bonde); WO 96/12193 (Bonde & Qvist); Ep 0718309 Al (Naser et al.); and WO 96/36645 (Eyre et al.).

Examples of type II collagen telopeptide assays for measuring cartilage resorption include WO 91/08478 (Eyre); WO 95/08115 (Qvist & Bonde); and WO 96/12193 (Bonde & Qvist).

Examples of type III collagen telopeptide assays include WO 88/08980 (Risteli & Risteli) and WO 91/08478 (Eyre).

The following patent disclosures are also of interest: U.S. Pat. No. 4,628,027 (Gay) discloses in vitro diagnostic methods using monoclonal antibodies against connective tissue proteins. U.S. Pat. No. 5,316,914 (Oshima et al.) discloses an enzyme sandwich immunoassay of human type III, IV, and VI collagens applicable to diagnosis of hepatic diseases. WO 94/14070 (Poole & Hollander) discloses an immunoassay for the measurement of collagen cleavage in cartilage. WO 94/18563 (Barrach et al.) discloses sandwich immunoassay methods for detecting type II collagen derived peptides associated with arthritis.

Of particular interest is the applicant's prior international publication, WO 91/0478, which discloses the following urinary resorption products of type II collagen:

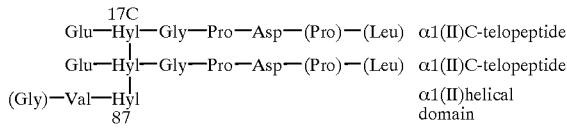

wherein the parentheses indicate optional amino acid residues, and the cross-linking residue depicted as Hyl-Hyl-Hyl is hydroxylysyl pyridinoline (HP), a natural 3-hydroxypyridinium residue present in mature collagen fibrils of various tissues. These analytes derive from the C-terminal cross-linked telopeptide domain of type II collagen and so are collectively referred to herein as "col2CTx".

The present disclosure also adopts the one-letter symbol form of amino acid shorthand; thus, the Glu-Hyl-Gly-Pro-Asp-(Pro)-(Leu) telopeptide components of the analytes shown above are referred to hereinafter as EKGPD (SEQ ID NO:1), EKGPDP (SEQ ID NO:2), and EKGPDPL (SEQ ID NO:3). Furthermore, as used herein the symbol "K" represents either lysine, in the case of linear peptides, or a cross-linking 3-hydroxypyridinium residue selected from among hydroxylysyl pyridinoline (HP) and lysyl pyridinoline (LP).

The applicant and colleagues have also described col2CTx in recent abstracts:

Eyre et al., Bone Miner. Res. 11(S1):S413, 1996, describes cross-linked telopeptides from collagen types I, II, and III in human urine.

Atley et al., Arth. Rheum. 40(9S):584, 1997, reports that RS-130830, a selective inhibitor of collagenase-3, blocks the release of hydroxyproline and a metalloproteinase (MMP) specific neoepitope, col2CTx, from bovine cartilage exposed to IL-1α.

Atley et al., Trans. Orthop. Res. Soc., New Orleans, 1998, reports matrix metalloproteinase-mediated release of immunoreactive telopeptides from cartilage type II collagen. The aim of this study was to evaluate whether an immunoassay based on a monoclonal antibody (mAb) 2B4, which recognizes a domain of the α1(II) C-telopeptide EKGPDP (SEQ ID NO:2), measures MMP cleavage products in cartilage. Referring to FIG. 1, mAb 2B4 recognizes the in vitro product of matrilysin digestion AFAGLGPREKGPDP (SEQ ID NO:4) of synthetic peptide AFAGLGPREKGPD-PLQYMRA (SEQ ID NO:5), but not AFAGLGPREKGPD-PLQ (SEQ ID NO:6) AFAGLGPREKGPDPLQY (SEQ ID NO:7), LQYMRA (SEQ ID NO:8), or YMRA (SEQ ID NO:9). The authors also noted detection of mAb 2B4 immunoreactivity in synovial fluid, serum, and urine. They concluded that this 2B4 epitope has the potential to be a useful marker of type II collagen resorption in vivo.

Moskowitz et al., Amer. Coll. Rheum., San Diego, Calif., Nov. 8–12, 1998, reports that the type II collagen C-telopeptide 2B4 epitope is a marker for cartilage resorption in familial osteoarthrosis.

Eyre et al., Combined Orthopaedic Research Societies Meeting, Vittel, France, Sep. 28–30, 1998, discusses biochemical markers of bone and collagen degradation, including a cross-linked telopeptide product of type II collagen degradation in urine (col2CTx).

In addition, monoclonal antibodies to the C-telopeptide of type II collagen as diagnostic markers for rheumatoid arthritis are reportedly under development at Osteometer Biotech A/S. BioWorld International, page 3, Dec. 3, 1997.

SUMMARY OF THE INVENTION

The invention provides improved assays for measuring type II collagen (cartilage) resorption in vivo. The subject immunoassays are useful for distinguishing between resorption of unmineralized cartilage and mineralized cartilage, and for measuring total cartilage resorption in vivo. The disclosed immunoassays employ either one or a combination of two antibodies. A first antibody binds to EKGPDP (SEQ ID NO:2) but not to EKGPDPLQ (SEQ ID NO:10), where the K symbols preferably refer to cross-linking 3-hydroxypyridinium residues. Measurement of analyte binding to the first antibody in serum provides an indication of unmineralized cartilage resorption in vivo.

A second antibody binds to EKGPDPLQ (SEQ ID NO:10) but not to EKGPDP (SEQ ID NO:2), where the K symbols also preferably refer to cross-linking 3-hydroxypyridinium residues. Measurement of analyte binding to the second antibody in serum provides an indication of mineralized cartilage resorption in vivo.

An indication of total (unmineralized and mineralized) cartilage resorption in vivo is provided by either measurement of analyte binding to the first antibody in urine, or by measurement of the total analyte binding to the first and second antibodies in serum.

The subject cartilage markers are preferably measured in conjunction with bone collagen resorption markers selected from among amino-terminal telopeptides of type I collagen, carboxy-terminal telopeptides of type I collagen, and free lysyl pyridinoline (deoxypyridinoline) cross-links.

DETAILED DESCRIPTION OF THE PREFERRED EMBODIMENT

The monoclonal antibody 2B4 recognizes a C-terminal epitope in the sequence EKGPDP (SEQ ID NO:2). The antibody requires the C-terminal proline to be free for any binding (i.e., Pro-COOH) and prefers K to be derivatized (e.g., cross-linked) through its side-chain (epsilon) amino group. The presence of extra amino acids C-terminal to the proline prevents mAb 2B4 binding to this peptide domain.

Various matrix metalloproteinases (MMPs) including collagenases (MMP1 and MMP13), gelatinases (MMP2 and 9), stromelysin (MMP3), and matrilysin (MMP7) can generate the mAb 2B4 epitope from cartilage type II collagen or a synthetic C-telopeptide domain (AFAGLGPREKGPDPLQYMRA(SEQ ID NO:5)). Matrilysin (MMP7) is the most potent based on in vitro studies with the recombinant enzymes.

Cathepsin K, however, is unable to cleave the P-L bond required for 2B4 epitope release, but generates a longer fragment, EKGPDPLQ(SEQ ID NO:10). This is significant because cathepsin K is a protease expressed essentially only by osteoclasts and is the key enzyme responsible for the resorption of the calcified collagen when osteoclasts resorb bone. Osteoclasts (or a very similar cell) are also responsible for degrading calcified cartilage. Calcified cartilage is formed transiently in the growth plates of growing animals and is also present in the adult skeleton at the interfaces between bone and cartilage in all types of joints. In arthritis, accelerated resorption and bony remodeling will result in extensive resorption of calcified cartilage by osteoclasts. This process can release into the bloodstream collagen type II C-telopeptides (EKGPDPLQ(SEQ ID NO:10)) that are not recognized by 2B4.

Since the urinary form of the type II collagen telopeptide analyte is EKGPDP (SEQ ID NO:2) or smaller, proteases in the kidney and/or liver remove the C-terminal -LQ before release into the urine. Therefore, two sources of immunoreactive col2CTx are defined: (1) direct generation by chondrocytes activated to degrade their matrix collagen by MMPs, and (2) secondary generation in the kidney and/or liver from the circulating products of osteoclastic resorption of calcified cartilage.

In arthritis (rheumatoid arthritis (RA) and osteoarthritis (OA)) MMPs are known to be key agents in the destruction of the collagenous matrices of joint cartilages. In both forms of arthritis, bone structure is also greatly affected. In RA, osteoporosis is a common consequence both directly from the disease process itself through the effects of inflammatory cytokines and as a side effect of corticosteroid therapy. The accelerated bone resorption will be most pronounced in involved joints and will include removal of the calcified cartilage underlying joint surfaces. In OA, osteophytes (bony outgrowths) often feature prominently in the joint pathology. Here, too, calcified cartilage will be formed and then degraded (the latter by osteoclasts) as part of osteophyte growth. Therefore to monitor and manage both major forms of arthritis it would be desirable to differentially measure MMP-mediated and osteoclast-mediated (cathepsin K) collagen type II destruction. In blood or synovial fluid, measuring col2CTx (EKGPDP (SEQ ID NO:2)) can index the former activity, whereas measuring the osteoclast product (EKGPDPLQ(SEQ ID NO:10)) can index the latter. In addition, urinary col2CTx can provide an index of total resorption (both unmineralized and mineralized cartilage). Such urine assays preferably include the steps of determining the creatinine content of the urine sample and correlating the ratio of the detected binding of the antibody to the creatinine content in order to provide a urinary index of total type II collagen resorption independent of urine volume.

The subject differential measurements of EKGPDP (SEQ ID NO:2) and EKGPDPLQ (SEQ ID NO:10) immunoreactivities have diagnostic value in the assessment of disease activity in the individual patient. In combination with measurement of a type I collagen marker to assess total bone resorption activity, and/or measurement of a type III collagen marker to assess other sources of non-mineralized connective tissue breakdown, an appropriate therapy can be prescribed and its desired effect monitored. Similarly, such differential assays can be used to identify new drug candidates (in vitro and in animals) and to provide surrogate markers in clinical trials for demonstrating desired beneficial effects on target tissues and cellular processes.

Representative assays for type I collagen resorption markers for this purpose include amino-terminal telopeptides of type I collagen (Osteomark®, Ostex International, Seattle, Wash.), carboxy-terminal telopeptides of type I collagen (CrossLaps®, Osteometer Biotech, Herlev, Denmark), and free lysyl pyridinoline cross-links (Pyrilinks®-D, Metra Biosystems, Mountain View, Calif.).

Representative assays for type III collagen resorption markers include amino-terminal telopeptides of type III collagen and carboxy-terminal telopeptides of type III collagen. Such assays are disclosed in U.S. Pat. No. 5,532,169, U.S. Pat. No. 5,641,687, and U.S. Pat. No. 06/010,862. Type III collagen resorption markers can be used to assess vascular collagen degradation (atherosclerosis), lung tissue degradation (e.g., emphysema and other destructive lung diseases), muscle wastage, frailty syndromes of the elderly, liver disease, hyperthyroidism, secondary effects of diabetes on connective tissue, and other inflammatory and infectious conditions that accelerate non-mineralized connective tissue breakdown.

Thus the invention provides, in a first embodiment, an improved method of analyzing a body fluid sample for the presence of an analyte indicative of a physiological condition, including the steps of contacting the body fluid sample with an antibody which binds to the analyte, detecting binding of the antibody in the body fluid sample, and correlating any detected binding to the physiological condition, the improvement comprising contacting a serum sample with an antibody which binds to

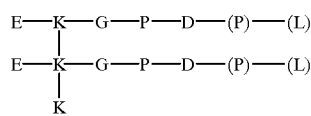

but not to

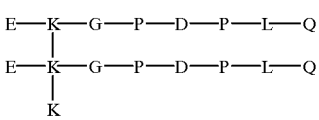

wherein K-K-K is hydroxylysyl pyridinoline or lysyl pyridinoline, and the parentheses represent optional amino acid residues, and correlating any detected binding to resorption of unmineralized type II collagen in vivo.

In a second embodiment, the invention provides an improved method of analyzing a body fluid sample for the presence of an analyte indicative of a physiological condition, including the steps of contacting the body fluid sample with an antibody which binds to the analyte, detecting binding of the antibody in the body fluid sample, and correlating any detected binding to the physiological condition, the improvement comprising contacting a serum sample with an antibody which binds to

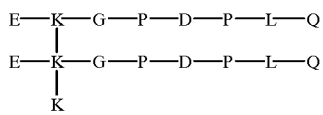

but not to

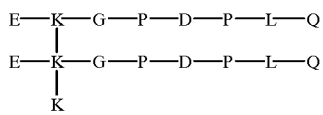

wherein K-K-K is hydroxylysyl pyridinoline or lysyl pyridinoline, and the parentheses represent optional amino acid residues, and correlating any detected binding to resorption of mineralized type II collagen in vivo.

In a third embodiment, the invention provides an improved method of analyzing a body fluid sample for the presence of an analyte indicative of a physiological condition, including the steps of contacting the body fluid sample with an antibody which binds to the analyte, detecting binding of the antibody in the body fluid sample, and correlating any detected binding to the physiological condition, the improvement comprising contacting a urine sample with an antibody which binds to

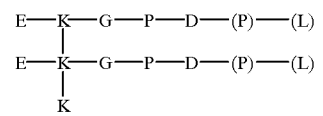

but not to

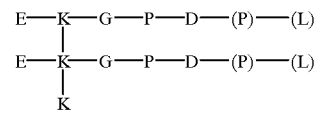

wherein K-K-K is hydroxylysyl pyridinoline or lysyl pyridinoline, and the parentheses represent optional amino acid residues, and correlating any detected binding to resorption of both unmineralized and mineralized type II collagen in vivo.

In a fourth embodiment, the invention provides an improved method of analyzing a body fluid sample for the presence of an analyte indicative of a physiological condition, including the steps of contacting the body fluid sample with an antibody which binds to the analyte, detecting binding of the antibody in the body fluid sample, and correlating any detected binding to the physiological condition, the improvement comprising contacting a serum sample with a first antibody which binds to

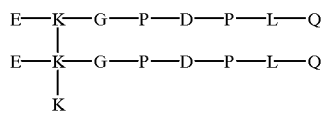

but not to

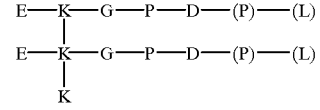

and contacting the serum sample with a second antibody which binds to

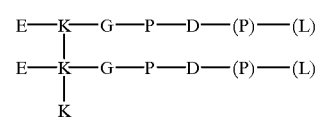

but not to

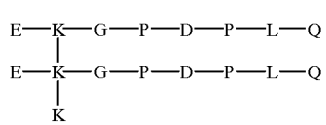

wherein K-K-K is hydroxylysyl pyridinoline or lysyl pyridinoline, and the parentheses represent optional amino acid residues, and correlating the total detected binding of the first and second antibodies to resorption of both mineralized and unmineralized type II collagen in vivo.

In a fifth embodiment, the invention provides an improved method of analyzing a body fluid sample for the presence of an analyte indicative of a physiological condition, including the steps of contacting the body fluid sample with an antibody which binds to the analyte, detecting binding of the antibody in the body fluid sample, and correlating any detected binding to the physiological condition, the improvement comprising contacting a serum sample with a first antibody which binds to

but not to

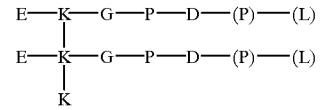

and contacting a urine sample with a second antibody which binds to

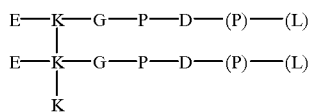

but not to

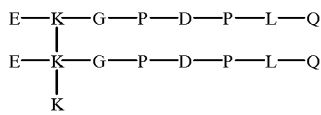

wherein K-K-K is hydroxylysyl pyridinoline or lysyl pyridinoline, and the parentheses represent optional amino acid residues, and correlating any detected binding of the first antibody to resorption of mineralized type II collagen in vivo, and any detected binding of the second antibody to resorption of both mineralized and unmineralized type II collagen in vivo.

The term "antibody" in this disclosure is meant to encompass polyclonal antibodies, monoclonal antibodies, and antigen-binding fragments thereof. Such EKGPDPLQ-binding (SEQ ID NO:10) and EKGPD(P)(L)-binding (SEQ ID NO:1–3) antibodies can be produced by standard methods well known in the art. A representative protocol follows.

EKGPDPLQ (SEQ ID NO:10) hybridoma development: Female RBF/DnJ mice are injected intraperitoneal (ip) with an emulsion of complete Freund's adjuvant and EKGPDPLQ (SEQ ID NO:10) synthetic peptide cross-linked to the carrier protein keyhole limpet hemacyanin (KLH) via glutaraldehyde (KLH-EKGPDPLQ). One month later a booster injection of KLH-EKGPDPLQ is given ip in an emulsion with incomplete Freund's adjuvant. Approximately eight weeks later the mice are sacrificed and splenocytes fused, by polyethylene glycol, to the FOX-NY murine myeloma cell line (ATCC CRL-1732). Fusion cells are grown in 96-well plates in selection media containing adenine, aminopterin and thymidine (AAT).

Approximately one week after fusion hybridoma colony culture supernatants are tested in ELISA for reactivity to the EKGPDPLQ (SEQ ID NO:10) synthetic peptide cross-linked via glutaraldehyde to bovine serum albumin (BSA-EKGPDPLQ). Hybridoma colonies producing antibody reactive with BSA-EKGPDPLQ are secondarily tested for specificity of reaction in ELISA against other synthetic peptide sequences. Among those tested are EKGPDP (SEQ ID NO:2) synthetic peptide cross-linked to BSA via glutaraldehyde (BSA-EKGPDP). Hybridoma colonies that react positively to BSA-EKGPDPLQ and negatively to BSA-EKGPDP are cryopreserved. Candidate hybridomas are cloned to monoclonality by the limited dilution method.

In competition ELISA, human serum specimens as well as soluble BSA-EKGPDPLQ are found to compete with solid phase BSA-EKGPDPLQ for candidate antibodies.

A cathepsin K digest of type II collagen can also be prepared for immunization and screening purposes. Proteoglycans are extracted from a tissue sample of human articular cartilage with a protein denaturant, such as 4 M guanidine HCl. The residue is washed with water and digested with recombinant cathepsin K (37° C., pH 5.8). The digest is fractionated by high performance liquid chromatography, for example by reverse phase, and fractions containing pyridinoline cross-links are monitored by fluorescence emission at 390 nm (297 nm excitation). The fluorescent fraction containing the cross-linked C-telopeptides of sequence EKGPDPLQ (SEQ ID NO:10) is identified by N-terminal sequence analysis. This fraction can be used for booster injection, for screening purposes and for validation of antibody specificity.

The subject antibodies can be employed in a wide variety of immunoassay formats that are well known in the art. For example, see: Harlow & Lane, Antibodies: A Laboratory Manual, Cold Spring Harbor Laboratory, pp. 553–612, 1988; Principles and Practice of Immunoassay, Price & Newman (Eds.), Stockton Press, 1991; and Immunoassay, Diamandis & Christopoulos (Eds.), Academic Press, 1996.

The entire disclosures of the prior scientific and patent publications cited in this patent application are incorporated by reference herein.

While the invention has been described in conjunction with preferred embodiments, one of ordinary skill after reading the foregoing specification will be able to effect various changes, substitutions of equivalents, and alterations to the subject matter set forth herein. Hence, the invention can be practiced in ways other than those specifically described herein. It is therefore intended that the protection granted by Letters Patent hereon be limited only by the appended claims and equivalents thereof.

The embodiments of the invention in which an exclusive property or privilege is claimed are defined as follows:

1. In a method of analyzing a body fluid sample for the presence of an analyte indicative of a physiological condition, comprising the steps of contacting the body fluid sample with an antibody which binds to the analyte, detecting binding of the antibody in the body fluid sample, and correlating any detected binding to the physiological condition, the improvement comprising contacting a serum sample with an antibody which binds to

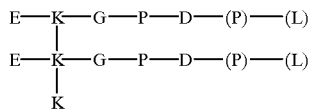

but not to

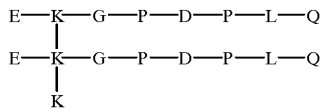

wherein K-K-K is hydroxylysyl pyridinoline or lysyl pyridinoline, and the parentheses represent optional amino acid residues, and correlating any detected binding to resorption of unmineralized type II collagen in vivo.

2. The method of claim 1, further comprising the step of contacting the serum sample with a second antibody which binds to a bone resorption marker selected from among amino-terminal telopeptides of type I collagen, carboxy-terminal telopeptides of type I collagen, and free lysyl pyridinoline cross-links, and correlating any detected binding of the second antibody in the sample to bone resorption in vivo.

3. The method of claim 1, further comprising the step of contacting the serum sample with a second antibody which binds to a type III collagen resorption marker selected from among amino-terminal telopeptides of type III collagen and carboxy-terminal telopeptides of type III collagen, and correlating any detected binding of the second antibody in the sample to type III collagen resorption in vivo.

4. In a method of analyzing a body fluid sample for the presence of an analyte indicative of a physiological condition, comprising the steps of contacting the body fluid sample with an antibody which binds to the analyte, detecting binding of the antibody in the body fluid sample, and correlating any detected binding to the physiological condition, the improvement comprising contacting a serum sample with an antibody which binds to

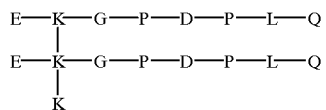

but not to

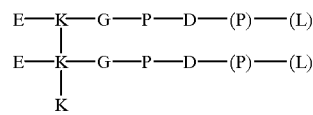

wherein K-K-K is hydroxylysyl pyridinoline or lysyl pyridinoline, and the parentheses represent optional amino acid residues, and correlating any detected binding to resorption of mineralized type II collagen in vivo.

5. The method of claim 4, further comprising the step of contacting the serum sample with a second antibody which binds to a bone resorption marker selected from among amino-terminal telopeptides of type I collagen, carboxy-terminal telopeptides of type I collagen, and free lysyl pyridinoline cross-links, and correlating any detected binding of the second antibody in the sample to bone resorption in vivo.

6. The method of claim 4, further comprising the step of contacting the serum sample with a second antibody which binds to a type III collagen resorption marker selected from among amino-terminal telopeptides of type III collagen and carboxy-terminal telopeptides of type III collagen, and correlating any detected binding of the second antibody in the sample to type III collagen resorption in vivo.

7. In a method of analyzing a body fluid sample for the presence of an analyte indicative of a physiological condition, comprising the steps of contacting the body fluid sample with an antibody which binds to the analyte, detecting binding of the antibody in the body fluid sample, and correlating any detected binding to the physiological condition, the improvement comprising contacting a urine sample with an antibody which binds to

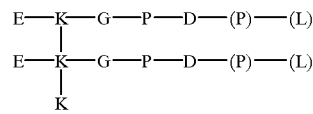

but not to

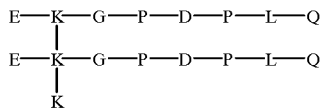

wherein K-K-K is hydroxylysyl pyridinoline or lysyl pyridinoline, and the parentheses represent optional amino acid residues, and correlating any detected binding to resorption of both unmineralized and mineralized type II collagen in vivo.

8. The method of claim 7, further comprising the steps of determining the creatinine content of the urine sample and correlating the ratio of the detected binding of the antibody to the creatinine content in order to provide a urinary index of total type II collagen resorption independent of urine volume.

9. The method of claim 7, further comprising the step of contacting the urine sample with a second antibody which binds to a bone resorption marker selected from among amino-terminal telopeptides of type I collagen, carboxy-terminal telopeptides of type I collagen, and free lysyl pyridinoline cross-links, and correlating any detected binding of the second antibody in the sample to bone resorption in vivo.

10. The method of claim 7, further comprising the step of contacting the urine sample with a second antibody which binds to a type III collagen resorption marker selected from among amino-terminal telopeptides of type III collagen and carboxy-terminal telopeptides of type III collagen, and correlating any detected binding of the second antibody in the sample to type III collagen resorption in vivo.

11. In a method of analyzing a body fluid sample for the presence of an analyte indicative of a physiological condition, comprising the steps of contacting the body fluid sample with an antibody which binds to the analyte, detecting binding of the antibody in the body fluid sample, and correlating any detected binding to the physiological condition, the improvement comprising contacting a serum sample with a first antibody which binds to

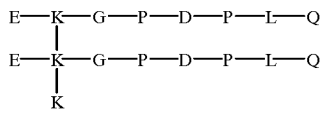

but not to

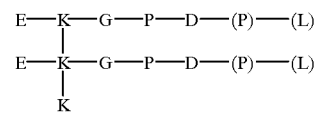

and contacting the serum sample with a second antibody which binds to

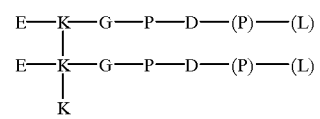

wherein K-K-K is hydroxylysyl pyridinoline or lysyl pyridinoline, and the parentheses represent optional amino acid residues, and correlating the total detected binding of the first and second antibodies to resorption of both mineralized and unmineralized type II collagen in vivo.

12. The method of claim 11, further comprising the step of contacting the serum sample with a third antibody which binds to a bone resorption marker selected from among amino-terminal telopeptides of type I collagen, carboxy-terminal telopeptides of type I collagen, and free lysyl pyridinoline cross-links, and correlating any detected binding of the third antibody in the sample to bone resorption in vivo.

13. The method of claim 11, further comprising the step of contacting the serum sample with a third antibody which binds to a type III collagen resorption marker selected from among amino-terminal telopeptides of type III collagen and carboxy-terminal telopeptides of type III collagen, and correlating any detected binding of the third antibody in the sample to type III collagen resorption in vivo.

14. In a method of analyzing a body fluid sample for the presence of an analyte indicative of a physiological condition, comprising the steps of contacting the body fluid sample with an antibody which binds to the analyte, detecting binding of the antibody in the body fluid sample, and correlating any detected binding to the physiological condition, the improvement comprising contacting a serum sample with a first antibody which binds to

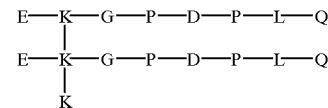

but not to

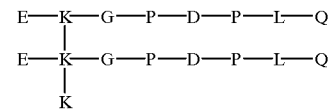

and contacting a urine sample with a second antibody which binds to

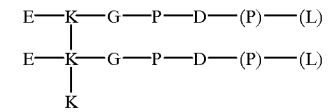

but not to

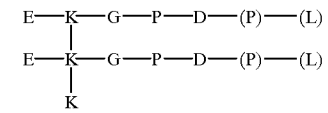

wherein K-K-K is hydroxylysyl pyridinoline or lysyl pyridinoline, and the parentheses represent optional amino acid residues, and correlating any detected binding of the first antibody to resorption of mineralized type II collagen in vivo, and any detected binding of the second antibody to resorption of both mineralized and unmineralized type II collagen in vivo.

15. The method of claim 14, further comprising the steps of determining the creatinine content of the urine sample and correlating the ratio of the detected binding of the second antibody to the creatinine content in order to provide a urinary index of total type II collagen resorption independent of urine volume.

16. The method of claim 14, further comprising the step of contacting at least one of the serum and urine samples with a third antibody which binds to a bone resorption marker selected from among amino-terminal telopeptides of type I collagen, carboxy-terminal telopeptides of type I collagen, and free lysyl pyridinoline cross-links, and correlating any detected binding of the third antibody in the sample to bone resorption in vivo.

17. The method of claim 14, further comprising the step of contacting at least one of the serum and urine samples with a third antibody which binds to a type III collagen resorption marker selected from among amino-terminal telopeptides of type III collagen and carboxy-terminal telopeptides of type III collagen, and correlating any detected binding of the third antibody in the sample to type III collagen resorption in vivo.

18. Synthetic peptide EKGPDPLQ (SEQ ID NO: 10).

* * * * *

SEQUENCE LISTING

```
<160> NUMBER OF SEQ ID NOS:   10

<210> SEQ ID NO 1
<211> LENGTH: 5
<212> TYPE: PRT
<213> ORGANISM: synthetic construct

<400> SEQUENCE: 1

Glu Lys Gly Pro Asp
1               5

<210> SEQ ID NO 2
<211> LENGTH: 6
<212> TYPE: PRT
<213> ORGANISM: synthetic construct

<400> SEQUENCE: 2
```

```
Glu Lys Gly Pro Asp Pro
1               5

<210> SEQ ID NO 3
<211> LENGTH: 7
<212> TYPE: PRT
<213> ORGANISM: synthetic construct

<400> SEQUENCE: 3

Glu Lys Gly Pro Asp Pro Leu
1               5

<210> SEQ ID NO 4
<211> LENGTH: 14
<212> TYPE: PRT
<213> ORGANISM: synthetic construct

<400> SEQUENCE: 4

Ala Phe Ala Gly Leu Gly Pro Arg Glu Lys Gly Pro Asp Pro
1               5                   10

<210> SEQ ID NO 5
<211> LENGTH: 20
<212> TYPE: PRT
<213> ORGANISM: synthetic construct

<400> SEQUENCE: 5

Ala Phe Ala Gly Leu Gly Pro Arg Glu Lys Gly Pro Asp Pro Leu Gln
1               5                   10                  15

Tyr Met Arg Ala
            20

<210> SEQ ID NO 6
<211> LENGTH: 16
<212> TYPE: PRT
<213> ORGANISM: synthetic construct

<400> SEQUENCE: 6

Ala Phe Ala Gly Leu Gly Pro Arg Glu Lys Gly Pro Asp Pro Leu Gln
1               5                   10                  15

<210> SEQ ID NO 7
<211> LENGTH: 17
<212> TYPE: PRT
<213> ORGANISM: synthetic construct

<400> SEQUENCE: 7

Ala Phe Ala Gly Leu Gly Pro Arg Glu Lys Gly Pro Asp Pro Leu Gln
1               5                   10                  15

Tyr

<210> SEQ ID NO 8
<211> LENGTH: 6
<212> TYPE: PRT
<213> ORGANISM: synthetic construct

<400> SEQUENCE: 8

Leu Gln Tyr Met Arg Ala
1               5

<210> SEQ ID NO 9
<211> LENGTH: 4
<212> TYPE: PRT
<213> ORGANISM: synthetic construct
```

```
<400> SEQUENCE: 9

Tyr Met Arg Ala
1

<210> SEQ ID NO 10
<211> LENGTH: 8
<212> TYPE: PRT
<213> ORGANISM: synthetic construct

<400> SEQUENCE: 10

Glu Lys Gly Pro Asp Pro Leu Gln
1               5
```